(12) United States Patent
Smith

(10) Patent No.: US 7,955,627 B1
(45) Date of Patent: Jun. 7, 2011

(54) ORGANIC COMPOSITIONS AND METHODS OF USE

(76) Inventor: Marlene M. Smith, Evanston, IL (US)

( * ) Notice: Subject to any disclaimer, the term of this patent is extended or adjusted under 35 U.S.C. 154(b) by 0 days.

(21) Appl. No.: 12/909,453

(22) Filed: Oct. 21, 2010

Related U.S. Application Data

(63) Continuation-in-part of application No. 12/399,228, filed on Mar. 6, 2009, now abandoned.

(60) Provisional application No. 61/034,858, filed on Mar. 7, 2008.

(51) Int. Cl.
*A01N 65/001* (2006.01)

(52) U.S. Cl. .......................................... 424/725
(58) Field of Classification Search .................. None
See application file for complete search history.

(56) References Cited

U.S. PATENT DOCUMENTS

| 6,706,298 | B1 | 3/2004 | Villagran et al. |
| 2009/0004334 | A1 | 1/2009 | Nair |

*Primary Examiner* — Michael V Meller
(74) *Attorney, Agent, or Firm* — Fay Sharpe LLP

(57) ABSTRACT

An organic composition comprising ginger, turmeric, cumin, fennel, cinnamon, red pepper, chia seed, celery seed, and hibiscus petals, preferably in a ratio of about 2:1:2:2:2:2:4:2:1, is disclosed. The composition is useful for treating and/or preventing certain physical ailments.

18 Claims, No Drawings

ORGANIC COMPOSITIONS AND METHODS OF USE

This application is a continuation-in-part application from U.S. patent application Ser. No. 12/399,228, filed Mar. 6, 2009, which claimed the benefit of U.S. Provisional Patent Application Ser. No. 61/034,858, filed Mar. 7, 2008. These applications are incorporated by reference in their entirety herein.

BACKGROUND

The present disclosure relates to organic compositions which provide relief from various physical ailments.

Several medications are known for use in pain relief, relieving bloated stomachs, suppressing appetite, and treating menopausal/premenstrual symptoms such as hot flashes. For example, ibuprofen and acetaminophen are used for general pain relief. However, some people are unable to take certain medications. Alternatively, some medications do not work for certain people. In addition, some medications have deleterious side effects. It is also desirable to have several options for treating a particular ailment.

BRIEF DESCRIPTION

Disclosed, in various embodiments, are organic compositions which provide relief from certain physical ailments. The organic compositions may comprise certain herbal extracts. Also disclosed are methods of using the organic compositions.

In embodiments, the organic composition comprises ginger, turmeric, cumin, fennel, cinnamon, and red pepper.

The volume ratio or weight ratio of ginger to turmeric to cumin to fennel to cinnamon to red pepper may be about 2:1:2:2:2:2.

The volume ratio or weight ratio of ginger to cumin, ginger to fennel, ginger to cinnamon, and/or ginger to red pepper, may be from about 1:0.8 to about 1:1.2.

The volume ratio or weight ratio of ginger to turmeric may be from about 3:1 to about 3:2.

The ginger, turmeric, cumin, fennel, and cinnamon may be in powder form and the red pepper may be in the form of flakes.

In additional embodiments, the organic composition comprises ginger, turmeric, cumin, fennel, cinnamon, red pepper, chia seed, celery seed, and hibiscus petals.

The volume ratio of ginger to turmeric to cumin to fennel to cinnamon to red pepper to chia seed to celery seed to hibiscus petals may be about 2:1:2:2:2:2:4:2:1.

The weight ratio of ginger to turmeric to cumin to fennel to cinnamon to red pepper to chia seed to celery seed to hibiscus petals may be about 2:1:2:2:2:2:4:2:1.

The organic composition may be useful for relieving pain in the joints, relieving stomach distension caused by an accumulation of gas in the stomach, suppressing the appetite, increasing physical endurance, and/or reducing the intensity or occurrence of hot flashes, when taken in therapeutically effective amounts.

These and other non-limiting characteristics are more particularly described below.

DETAILED DESCRIPTION

The numerical values in the specification and claims of this application should be understood to include numerical values which are the same when reduced to the same number of significant figures and numerical values which differ from the stated value by less than the experimental error of conventional measurement techniques of the type described in the present application to determine the value.

The present disclosure may be understood more readily by reference to the following detailed description of preferred embodiments and the examples included herein.

The modifier "about" used in connection with a quantity is inclusive of the stated value and has the meaning dictated by the context (for example, it includes at least the degree of error associated with the measurement of the particular quantity). When used with a specific value, it should also be considered as disclosing that value. For example, the term "about 1:2" also discloses the value "1:2" and the term "from about 2 to about 4" also discloses the range "from 2 to 4."

The organic compositions of the present disclosure comprise ginger, turmeric, cumin, fennel, cinnamon, red pepper, chia seed, celery seed, and hibiscus petals. Each of the ingredients is known to be edible and is used as a spice in various foods. It is believed that the combination of these ingredients act synergistically to relieve various physical ailments. For example, turmeric and red pepper have been known to be used for treating arthritis and/or inflammation. As another example, fennel and cinnamon have been known to be used to relieve gas, bloating, and stomach pains. However, their combination appears to provide greater relief than either one separately.

The ginger, cumin, fennel, cinnamon, and red pepper are generally present in the organic composition in roughly equal amounts. They can vary by roughly 20 percent from each other. Put in other words, using ginger as the base amount, the ratio of ginger to cumin may be from about 1:0.8 to about 1:1.2. The same values hold for the ratio of ginger to fennel, ginger to cinnamon, and ginger to red pepper. These ratios can be either by volume or by weight.

The turmeric is present generally present at about half the amount of the other ingredients. However, it can vary as well. Using ginger as the base amount, the ratio of ginger to turmeric may be from about 3:1 to about 3:2. In specific embodiments, the ratio of ginger to turmeric is about 2:1. Again, the ratio can be either by volume or by weight.

The chia seed, celery seed, and hibiscus petals are also present in some different formulations. Using ginger as the base amount, the ratio of ginger to chia seed is from about 1:3 to 1:5. The ratio of chia seed to celery seed is from about 3:1 to about 3:2. The ratio of chia seed to hibiscus petals is from about 5:1 to about 3:1. The ratio of celery seed to hibiscus petals is from about 3:1 to about 3:2. Again, these ratios can be either by volume or weight.

In specific embodiments, the volume ratio or weight ratio of ginger to turmeric to cumin to fennel to cinnamon to red pepper is about 2:1:2:2:2:2.

In additional specific embodiments, the volume ratio or weight ratio of ginger to turmeric to cumin to fennel to cinnamon to red pepper to chia seed to celery seed to hibiscus petals is about 2:1:2:2:2:2:4:2:1.

The ginger, turmeric, cumin, fennel, cinnamon, and red pepper are generally mixed together in dry form. Typically, the ginger, turmeric, cumin, fennel, cinnamon, chia seed, and hibiscus petals are in powder form, while the red pepper is present in the form of flakes. The celery seeds, which can also be considered a small fruit, can be used in the seed form or also as a powder. However, the form can vary. For example, their extracts may be used. Extracts may be prepared by, for example, using supercritical carbon dioxide with the plant to obtain an oil extract and an oil-free residue. Alternatively, the plant can be extracted in a water/alcohol mixture, wherein the water and alcohol are then evaporated to obtain a powdered residue. As another example, the ingredients may be liquefied. In certain embodiments, the organic compositions of the present disclosure consist essentially of these ingredients and in other embodiments, consist of these six ingredients.

The organic composition is useful in treating several different ailments. When consistently taken by a person, it provides pain relief in the joints, such as the knees and hips, especially after high impact activities like running, tennis, biking, and jumping rope. Decreased stiffness and aching has been noticed. It relieves stomach distension caused by the accumulation of stomach gas, which can happen after eating various foods and/or drinking various beverages. When the organic composition is taken at the time of stomach distension or afterwards, the stomach gas appears to dissipate more easily. When taken consistently, stomach gas appears not to occur at all. In addition, the organic composition can act as an appetite suppressant.

Additional beneficial effects have been noted. Physical endurance may increase, allowing exercise for longer durations and decreased recovery time afterwards (i.e. less fatigue noticed). The intensity and/or occurrence of "hot flashes" is also decreased when the organic composition is taken consistently.

The organic composition is generally administered orally (i.e. ingested). For example, the organic composition may be placed in size 00 capsules (having a volume of approximately 0.9-1.0 mL). However, it is possible that it could also be administered parenterally.

Solid dosage forms for oral administration include capsules, tablets, pills, powders, and granules. The organic composition may be further mixed with other inert ingredients, excipients, or carriers such as corn starch, lactose, gelatin, glycerol, milk sugar, high molecular weight polyethylene glycols, and the like. The solid dosage forms of tablets, capsules, pills, and granules can be prepared with coatings and shells such as enteric coatings and other coatings well-known in the pharmaceutical formulating art. They may also be of a composition such that they release the active ingredient(s) only, or preferentially, in a certain part of the intestinal tract or in a delayed manner.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water, ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, polyethylene glycols, fatty acid esters of sorbitan, and mixtures thereof. Besides inert diluents, the oral compositions may also include adjuvants such as wetting agents, emulsifying and suspending agents, sweetening, flavoring and perfuming agents.

The organic composition can be generally administered in a daily dosage of about 2000 mg per day. However, the amount may vary as needed. Actual dosage levels and the mode of administration can be varied in order to achieve the effective therapeutic response for a particular patient. The phrase "therapeutically effective amount" means a sufficient amount of the composition to treat disorders, at a reasonable benefit/risk ratio applicable to any medical treatment. The specific therapeutically effective dose level for any particular patient will depend upon a variety of factors including the ailment being treated and the severity of the ailment; medical history of the patient, age, body weight, general health, sex and diet of the patient, the time of administration, route of administration, the duration of the treatment, and the like.

The following examples are provided to illustrate the compositions and methods of the present disclosure. The example is merely illustrative and is not intended to limit the disclosure to the materials, conditions, or process parameters set forth therein.

Example 1

The following ingredients were mixed together to form an organic composition:
  2 teaspoons of powdered ginger root, for a total of 10 grams or 0.706 oz;
  1 teaspoon powdered turmeric root, for a total of 5 grams or 0.353 oz;
  2 teaspoons powdered cumin seeds, for a total of 10 grams or 0.706 oz;
  2 teaspoons powdered fennel seed, for a total of 10 grams or 0.706 oz;
  2 teaspoons powdered cinnamon, for a total of 10 grams or 0.706 oz; and
  2 teaspoons red pepper flakes, for a total of 10 grams or 0.706 oz.

The composition was placed in size "00" capsules. Two capsules were taken twice a day, once in the morning and once in the evening. There was approximately 500 mg of the composition in each capsule.

Prophetic Example 2

The following ingredients are mixed together to form an organic composition:
  2 teaspoons of powdered ginger root, for a total of 10 grams or 0.706 oz;
  1 teaspoon powdered turmeric root, for a total of 5 grams or 0.353 oz;
  2 teaspoons powdered cumin seeds, for a total of 10 grams or 0.706 oz;
  2 teaspoons powdered fennel seed, for a total of 10 grams or 0.706 oz;
  2 teaspoons powdered cinnamon, for a total of 10 grams or 0.706 oz;
  2 teaspoons red pepper flakes, for a total of 10 grams or 0.706 oz;
  4 teaspoons chia seed powder, for a total of 20 grams or 1.412 oz;
  2 teaspoons celery seeds, for a total of 10 grams or 0.706 oz; and
  1 teaspoon hibiscus petal powder, for a total of 5 grams or 0.353 oz.

The composition is placed in size "00" capsules. Two capsules are taken twice a day, once in the morning and once in the evening. There is approximately 500 mg of the composition in each capsule.

The organic compositions of the present disclosure have been described with reference to exemplary embodiments. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

The invention claimed is:

1. A composition for pain relief in a person, comprising therapeutically effective amounts of powdered ginger, powdered tumeric, powdered cumin, powdered fennel, powdered cinnamon, red pepper flakes, powdered chia seed, powdered celery seed, and powdered hibiscus petals, wherein the volume ratio of ginger to tumeric to cumin to fennel to cinnamon to red pepper to chia seed to celery seed to hibiscus petals is about 2:1:2:2:2:2:4:2:1.

2. The composition of claim 1, wherein the volume ratio of ginger to cumin is from about 1:0.8 to about 1:1.2.

3. The composition of claim 1, wherein the volume ratio of ginger to turmeric is from about 3:1 to about 3:2.

4. The composition of claim 1, wherein the volume ratio of ginger to fennel is from about 1:0.8 to about 1:1.2.

5. The composition of claim 1, wherein the volume ratio of ginger to cinnamon is from about 1:0.8 to about 1:1.2.

6. The composition of claim 1, wherein the volume ratio of ginger to red pepper is from about 1:0.8 to about 1:1.2.

7. The composition of claim 1, wherein the volume ratio of ginger to chia seed is from about 1:3 to about 1:5.

8. The composition of claim 1, wherein the volume ratio of chia seed to celery seed is from about 3:1 to about 3:2.

9. The composition of claim 1, wherein the volume ratio of chia seed to hibiscus petals is from about 5:1 to about 3:1.

10. The composition of claim 1, wherein the volume ratio of celery seed to hibiscus petals is from about 3:1 to about 3:2.

11. A composition for pain relief in a person, comprising therapeutically effective amounts of powdered ginger, powdered tumeric, powdered cumin, powdered fennel, powdered cinnamon, red pepper flakes, powdered chia seed, powdered celery seed, and powdered hibiscus petals, wherein the weight ratio of ginger to tumeric to cumin to fennel to cinnamon to red pepper to chia seed to celery seed to hibiscus petals is about 2:1:2:2:2:2:4:2:1.

12. The composition of claim 11, wherein the weight ratio of ginger to turmeric is from about 3:1 to about 3:2.

13. The composition of claim 11, wherein the weight ratio of ginger to fennel is from about 1:0.8 to about 1:1.2.

14. The composition of claim 11, wherein the weight ratio of ginger to cinnamon is from about 1:0.8 to about 1:1.2.

15. The composition of claim 11, wherein the weight ratio of ginger to red pepper is from about 1:0.8 to about 1:1.2.

16. The composition of claim 11, wherein the weight ratio of chia seed to celery seed is from about 3:1 to about 3:2.

17. The composition of claim 11, wherein the weight ratio of chia seed to hibiscus petals is from about 5:1 to about 3:1.

18. The composition of claim 11, wherein the weight ratio of ginger to cumin is from about 1:0.8 to about 1:1.2.

* * * * *